United States Patent [19]

Nazarian

[11] Patent Number: 5,558,790
[45] Date of Patent: Sep. 24, 1996

[54] METHOD AND LASER SYSTEM FOR THE THERMAL ANALYSIS OF A SUBSTANCE

[75] Inventor: Ashot Nazarian, Gaithersburg, Md.

[73] Assignee: Science Applications International Corporation, San Diego, Calif.

[21] Appl. No.: 196,491

[22] Filed: Feb. 15, 1994

[51] Int. Cl.⁶ .......................... B23K 26/00; G01N 25/18; G01N 25/20
[52] U.S. Cl. .......................... 219/121.77; 374/43; 374/44
[58] Field of Search .......................... 219/121.76, 121.77, 219/121.85; 374/15, 33, 36, 43, 10, 11, 44, 34, 41; 436/147, 157; 250/339.01, 339.03, 339.04, 341.7; 374/55

[56] References Cited

U.S. PATENT DOCUMENTS

| | | |
|---|---|---|
| 3,847,546 | 11/1974 | Paul . |
| 3,892,125 | 7/1975 | Nunogaki .................... 374/43 |
| 4,122,409 | 10/1978 | Marlett et al. . |
| 4,126,032 | 11/1978 | Ikeda et al. ................... 374/10 |
| 4,504,951 | 3/1985 | McMahan et al. . |
| 4,817,020 | 3/1989 | Chande et al. ............ 250/339.04 |
| 4,865,461 | 9/1989 | Taylor et al. ................ 374/55 |
| 4,928,254 | 5/1990 | Knudsen et al. ............. 374/43 |
| 5,441,343 | 8/1995 | Pylkki et al. ............... 374/44 |

FOREIGN PATENT DOCUMENTS

| | | | |
|---|---|---|---|
| 64-16954 | 1/1989 | Japan ........................ | 374/43 |
| 1-313747 | 12/1989 | Japan ........................ | 374/43 |
| 124117 | 3/1986 | U.S.S.R. . | |
| 1597068 | 6/1990 | U.S.S.R. . | |

*Primary Examiner*—Geoffrey S. Evans
*Attorney, Agent, or Firm*—Pretty, Schroeder, Brueggemann & Clark

[57] ABSTRACT

Provided is a method and apparatus for the thermal analysis of a substance. The method comprises suspending a substance sample on a substrate in a reactor using a temperature sensor positioned at the center of the reactor. The reactor is then heated by two laser beams focused on the reactor. The resulting temperature dependence of the sample/substance during heating is measured. Additionally, the sample/substrate is heated to a temperature above the reactor temperature with a third laser beam. The rate at which the sample/substance temperature relaxes to the temperature of the reactor is measured. This additional heating of the sample/substance is preferably achieved by a laser focused on the sample/substance itself. All of the measured information can then be fed into a computer through an electronic interface to provide data on the particular substance undergoing thermal analysis. The method and the system used to effect the practice of the method can be used to study samples of various substances to aid in the design and process control of manufacturing processes through integration with a neural network. The method has also been demonstrated to provide data necessary to optimize the burning of high sulfur fuel oils. The present invention is particularly applicable to aiding in the analysis and design of thermal processes used to destroy hazardous chemicals in waste materials.

40 Claims, 8 Drawing Sheets

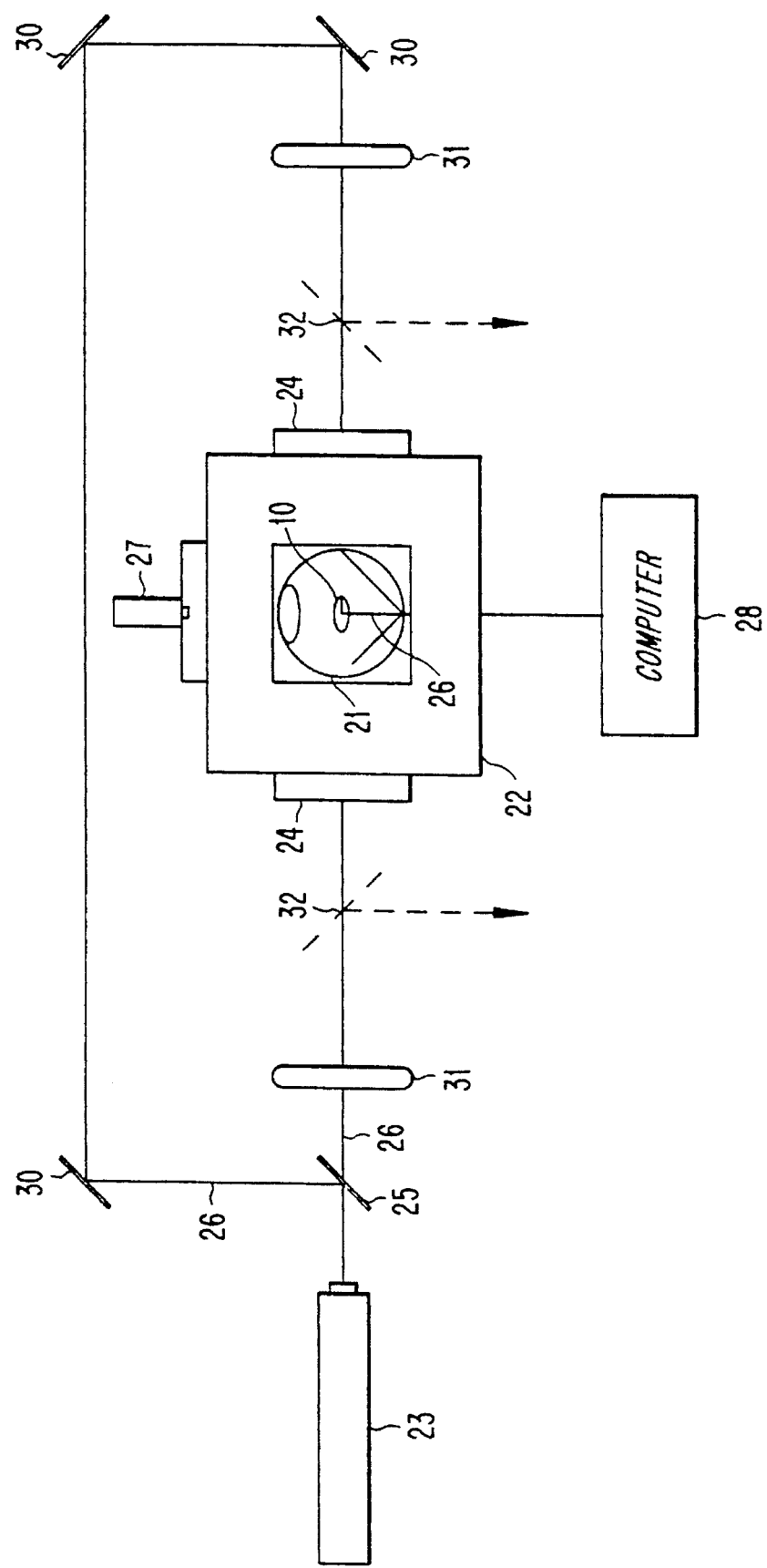

METHOD AND LASER SYSTEM FOR THE THERMAL ANALYSIS OF A SUBSTANCE

BACKGROUND OF THE INVENTION

The present invention relates to a method and system for the thermal analysis of a substance. Lasers play an important role in the thermal analysis, lending to its accuracy and expediency. The method and system of the present invention can be used in many technical applications, e.g., the destruction of hazardous waste material.

Methods and systems for the thermal analysis of various materials are well known in the art. For example, see U.S. Pat. No. 3,847,546 which discloses a temperature programmed solid sample chamber. The chamber is adapted to apply thermal energy to a sample material. The carrier gases flow through the chamber whose temperature is raised at a programmed, relatively slow rate to limit the thermal energy applied to the sample. The effluent gases containing the decomposition products are swept through a first detector and then through a first valve to a vent. After storage, the effluent gases are then passed through a second detector. The information obtained from the two detectors is used to analyze the particular substance under investigation.

The accuracy and reproducibility of the information obtained has often been a problem with prior art thermal analysis techniques. When wanting to study the actual chemical/physical process a substance undergoes during thermal degradation, the prior art analyses have also been quite deficient in their ability to accurately obtain data which can be used in an appropriate analysis.

The rate of the energy exchange during chemical/physical processes is usually measured in a reactor. It is determined either from the rate of change of sample weight, or by measurement of the thermal currents from the sample caused by heat evolution or absorption during this process. For a number of chemical/physical processes (thermal destruction, incineration, evaporation and phase transfer) the important property of the reactor is the rate of change of the temperature therein. If the reactor temperature rises slowly, the chemical process can finish before the temperature region of interest is reached. Accordingly, for rapid sample heating, the present inventor developed a laser device and a laser control device as described in the U.S.S.R. Certificate of Invention S.U. No. 124117, which is hereby incorporated by reference. The reactor permits one to achieve more efficient and accurate measurements, thereby expanding its potential practical applicability.

Indeed, increasing attention is being paid to the treatment of hazardous waste through thermal destruction. Among the preferred technologies are thermal processes that de-toxify and reduce the volume of hazardous wastes by exposing them to appropriate thermal regimes. However, as with any technology, there are potential problems which may detract from the application of the technology. Environmental pollution from particulate matter and off-gases can occur. Therefore, if practical, efficient and accurate, a suitable thermal analysis system and method could play a very important role in the development of hazardous waste treatment technology by permitting one to determine the parameters and conditions of appropriate thermal processes.

The laser used in such a thermal reactor can also be monitored and controlled by an intensity control system to aid in the uniformity of the heating of the sample substance, and hence improving the accuracy and usefulness of the information subsequently obtained. Such laser intensity and control systems are well known. For example, see U.S. Pat. No. 4,122,409; U.S. Pat. No. 4,504,951; as well as the inventor's own U.S.S.R. Certificate of Invention S.U. No. 1,597,068, which is hereby incorporated by reference.

Yet, the application of such methods and systems to many technical fields still requires an improvement in the measurement techniques, the accuracy of the information obtained and the usefulness of the information obtained, for the application to be of practical significance. Technical applications such as the treatment of waste materials would dearly welcome the existence of a practical and useful thermal analysis method and system.

Accordingly, it is an object of the present invention to provide a novel and improved method for the thermal analysis of a substance, such as waste material, liquid fuels, coal and others.

Yet another object of the present invention is to provide a novel system for use in said method of thermal analysis.

Yet another object of the present invention is to provide a method and system for the thermal analysis of a sample substance which would be readily applicable for many technical processes, and in particular waste treatment.

These and other objects of the present invention will become apparent upon a review of the following specification, the Figures of the Drawing, and the claims appended thereto.

SUMMARY OF THE INVENTION

In accordance with the foregoing objectives, there is provided by the present invention a method for the thermal analysis of a sample substance. The method comprises placing a sample of a substance on a thermally conductive substrate in a reactor, with the substrate being suspended on a temperature sensor and positioned at the center of the reactor. The reactor is then heated with laser beams of equal intensity from opposing sides. The temperature of the reactor and the temperature of the gas within the reactor are measured during the heating. Additionally, it is an important feature of the present invention that the sample/substrate combination is heated to a temperature above the reactor temperature, with the rate at which the temperature of the combination relaxes back to the reactor temperature then being measured. This latter technique most accurately and easily provides an important piece of information which permits one to analyze the information obtained from the other measurements in a more accurate and useful manner.

All of the measured information can be fed into a computer through an electronic interface to provide data on the particular substance undergoing thermal analysis in any form desirable. The data can also be used to effect changes in an ongoing process. For example, the method and system used to effect the practice of the method can be used to study samples of various substances to aid in the design and process control of manufacturing processes through integration with a neural network.

In a preferred embodiment, the reactor is spherical and the substrate is of a circular shape, with the ratio of the diameter of the spherical reactor to the ratio of the diameter of the substrate/sample being greater than 2.5. Such a ratio has been surprisingly found to be important to ensure uniform heating of the reactor and its environment, and hence the sample/substrate within the reactor, when using the method and system of the present invention.

In another embodiment of the present invention, the method of the present invention is applicable to a process for controlling the incineration of waste. The process involves thermally analyzing a sample of the waste to be incinerated by the method of the present invention. Using the information from the thermal analysis permits one to more appropriately design the temperature regime of the incineration to provide a more efficient and effective overall process. In a more preferred embodiment, off-gases created during the heating of the sample are also analyzed by conventional means, such as a gas chromatograph, to provide information as to what gases are actually created during the temperature degradation of the sample. Using this information in conjunction with the thermal analysis of the substance allows one to not only design a more efficient incineration process, but also to design a process which is environmentally friendly. The present invention is particularly applicable, therefore, to the design of thermal processes used to destroy hazardous chemicals contained in waste materials. The present invention has also been found particularly applicable to processes involving the burning of high sulfur fuel oils.

BRIEF DESCRIPTION OF THE DRAWING

FIG. 2A is a schematic of a system useful in the practice of the present invention.

DETAILED DESCRIPTION OF THE PREFERRED EMBODIMENTS

Figure 1:
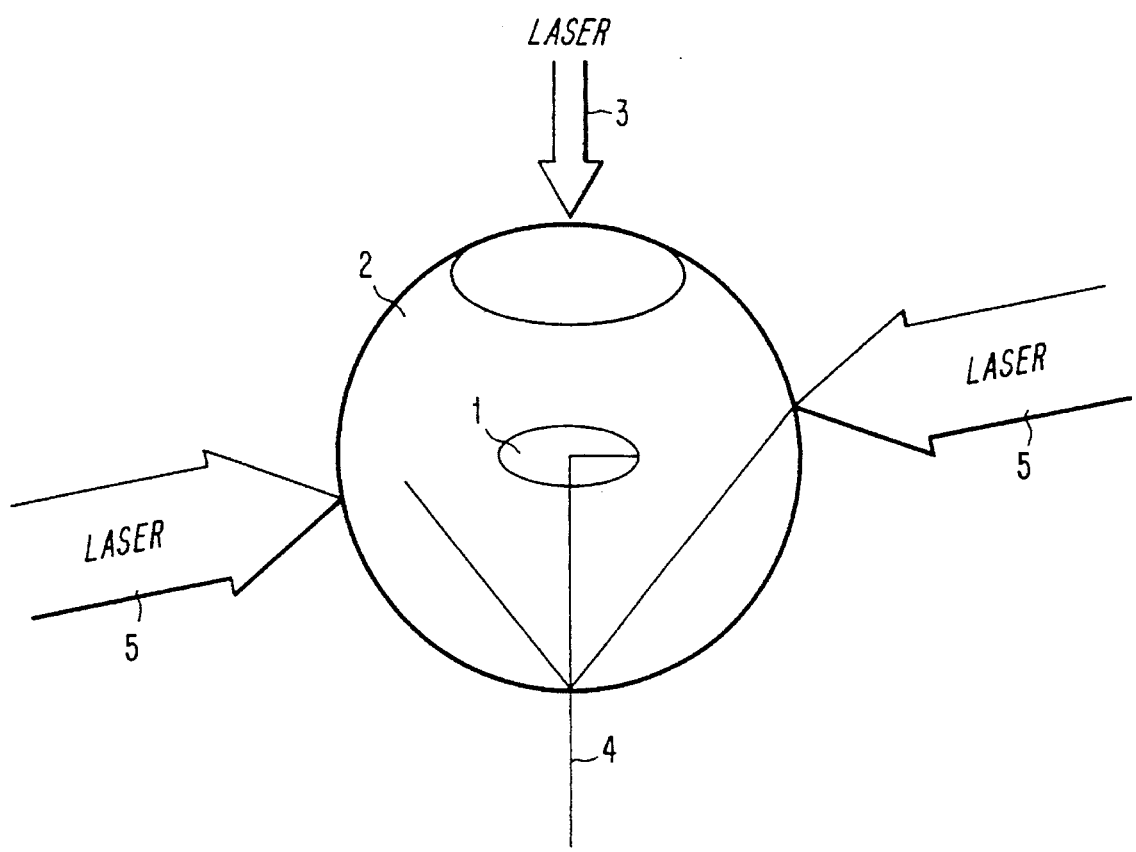
FIG. 1 is a schematic of a reactor as used in the practice of the method and system of the present invention.

In describing the preferred embodiments of the method and system of the present invention, reference is made to FIG. 1 of the drawing. The preferred method involves placing a sample of a substance to be analyzed on a substrate 1 in a reactor 2 with the substrate being suspended on a temperature sensor 4. The substrate is positioned at the center of the reactor. The reactor is preferably spherical and the substrate is preferably of a circular shape. These shapes have been found most convenient for assuring that one obtains an even heat field around the sample, and thereby a sample which is uniformly heated. It is most preferred, however, that the ratio of the diameter of the spherical reactor to the ratio of the diameter of the circular substrate/sample combination is greater than 2.5. It has been found that when the ratio of diameters is within this range, a uniform heat field around the sample is generally obtained.

The substrate can be made of any thermal conductive material, which assures uniform heating. While the substrate shown in FIG. 1 is of a circular shape on which the sample of the substance is placed, the substrate can also be the end of a temperature probe on which the sample material is simply suspended. This works particularly well for extremely small samples of a substance to be analyzed. In FIG. 1, the temperature probe is attached to the circular substrate 1. Thus, in measuring the temperature of the sample, it is the temperature of the sample/substrate which is actually being measured for practical reasons. Therefore, for the purposes of the present description, wherever the phrase "sample/substrate" is used, it is to be understood that reference is being made to the sample and substrate in combination as it is the temperature of each which raises due to the energy of the additional heating.

The construction of the sphere is such that the composition is of a material which preferably fulfills the relationship $\beta/\alpha > 1$, where $\beta$ is a coefficient of spectral adsorption at the fixed wavelength of the lasers being used to heat the reactor, and $\alpha$ is the integral hemispherical emissivity. Meeting this particular relationship has been found to permit a more accurate measurement, and hence provide more useful information. From a practical standpoint, the reactor is preferably comprised of an oxidized copper/nickel material, or other material found to meet the above recited relationship. In conjunction with the foregoing relationship, it is also preferred that the substrate is comprised of copper or nickel.

The temperature sensor 4 is structured so as to be able to measure the temperature of the reactor wall, the environmental gases within the reactor, and the substrate/sample. All of these measurements are taken during the heating of the reactor containing the sample.

The heating is achieved by the use of laser beams 5 which are of equal intensity and are focused upon the reactor from opposing sides. To ensure their equal intensity it is most preferred that a single laser beam be split and passed through a system of mirrors and lenses focused upon the opposing sides of the reactor. For the purposes of the present invention, it is most preferred that the laser beams used are of a wavelength in the range of from 1.055 to 1.065 microns for a reactor comprised of oxidized copper and nickel. Such a suitable laser would be, for example, a neodymium laser. The use of such a laser in connection with an oxidized copper/nickel reactor is most preferred.

A most important feature of the present invention is the use of an additional laser beam 3 focused directly upon the sample/substrate combination. This additional laser beam 3 heats the sample/substrate to a temperature above the reactor temperature, with the rate at which the sample/substrate temperature relaxes to the reactor temperature being measured. Generally, the sample/substrate only needs to be heated in the range of from about 10° K. to 50° K. above the reactor temperature to achieve sufficient information by employing this technique. It is, however, preferred that the temperature be raised at least 10° K. By using the additional laser beam and heating the sample/substrate in order to measure the rate at which the sample/substrate temperature relaxes, one is able to accurately and efficiently obtain enough information to determine the heat loss parameter for the system. Feeding all of the measurements, therefore, into a computer through an electronic interface can provide very important information.

For example, a heat balance on the sample yields the following:

$$C_p M dt/dt = -C_p M \lambda (T-T_o) + M_s q(T) \tag{1}$$

where T is the sample temperature, $T_o$ is the temperature of the surrounding gas and $\lambda$ is a heat loss parameter. The rate of heat evolution due to the reaction is q(T), with $C_p$ and M being the specific heat capacity and mass of the sample with substrate, respectively. The mass of the sample is denoted by $M_s$. The use of the laser beam 3 permits an independent determination of the heat loss in order to ascertain the parameter, $\lambda$, by measuring the rate at which the sample temperature relaxes to the reactor temperature after laser heating. The heat loss (F) is equal to $\lambda (T-T_o)$. Therefore, by ascertaining the heat loss and measuring T and $T_o$, one can easily ascertain the heat loss parameter $\lambda$.

Figure 2B:
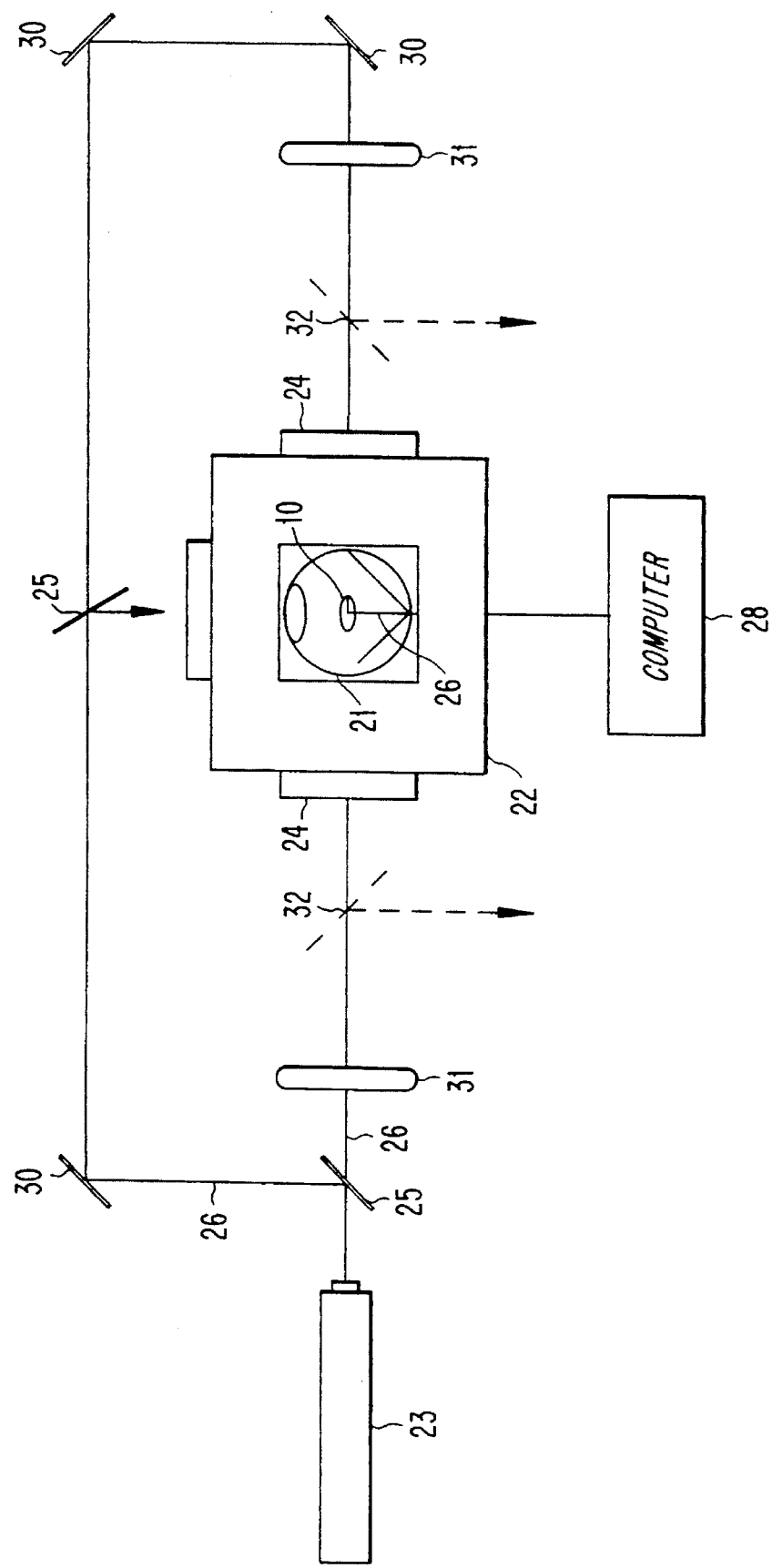
FIG. 2B is another schematic of a different system useful in the practice of the present invention.

A preferred embodiment of a laser driven thermal reactor for use in the present invention is depicted in FIGS. 2A and 2B. A disk-shaped substrate 10 is contacted by a temperature sensor 20 inside sphere-reactor 21. The assembly is mounted in a chamber 22 and heated by an infrared laser (Nd:YAG) 23 from opposing sides 24 to achieve uniform temperatures. The characteristic diameter of the substrate is a few millimeters. The substrate width is far smaller than its diameter. The output beam of the laser 23 is divided by a beam splitter 25 to yield two opposing beams 26 of equal intensity.

By simultaneous temporally resolved measurements of the sphere and gas temperatures, parameters of evaporation and the rate of heat evolution could be recovered. Each beam is directed to the sphere by a mirror 30 and lens 31 system. The laser beams are diverted with movable mirrors 32 placed immediately before the chamber so that their intensities can be measured. By displacing the focusing lenses along the beam axes, the spot size can be matched to that of the reactor.

The heating of the sample/substrate directly is generally achieved by use of an additional laser 27 (FIG. 2A), or by further splitting the beam of laser 23 (FIG. 2B). This laser 27 is preferably situated above the sample/substrate combination and is focused directly upon the sample/substrate. The power of the laser, however, need only be sufficient to raise the temperature of the sample/substrate from 10° K. to 50° K., or at least 10° K. above the existing temperature, which can be up to 2000° K. It is also preferred that the laser 27 be of the same wavelength as that of laser 23. The chamber is generally filled with gas ($N_2$, $O_2$) or air. The gas pressure is chosen so as to exclude convective flow (typically <30 kPa). During heating, the signal from the temperature sensor 20 .and its time derivative is read into a computer 28 through an electronic interface. A device for stabilization and control of the laser intensity can also be used in order to permit one to achieve more efficient and accurate measurements.

Figure 3:
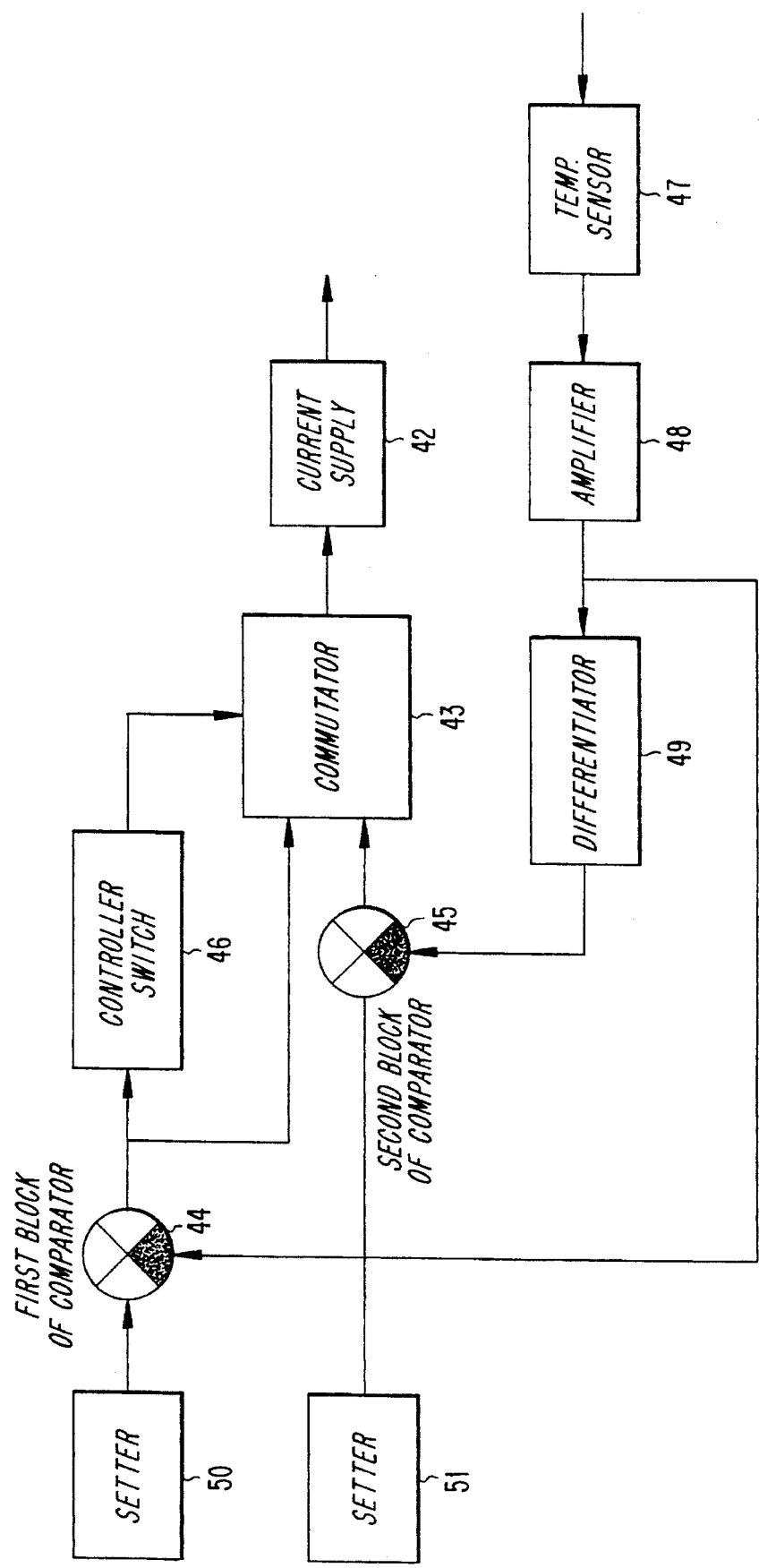
FIG. 3 is a schematic of a stabilization and control device useful in the practice of the present invention.

A schematic of one suitable stabilization and control device is shown in FIG. 3. In operation, initially, the second block of comparator 45 is connected to the current supply 42 by commutator 43. The controlled current supply is switched off. The setter 50 gives the necessary temperature level of the sample/substrate whereas setter 51 governs the rate of temperature increase. Next, the controlled current supply for the laser is switched on. The set point signal from setter 51 is input to the second block of comparator 45. The comparator output drives commutator 43 which in turn controls the laser current supply. This sequence initiates heating of the sample/substrate by the laser. The signal from the temperature sensor 47 is amplified 48 then differentiated 49 and compared with the specified rate of temperature increase 45. The difference of signals through commutator 43 is subtracted from the controlled current supply to alter the laser beam intensity and thereby provide the necessary rate of temperature increase. At the same time, the amplified signal from the detector 47 is input to the first block of comparator 44 where it is compared with the set point temperature of setter 50. Until the temperature of the sample is lower than the necessary level, the output signal from the first block of comparator remains non-zero.

After reaching the necessary temperature of the sample/substrate, the latter signal becomes null and another signal from controller switch 46 is input to commutator 43. The commutator reaches the temperature setpoint when the signal from the first block of comparator 44 is equal to the controlled current supply.

Use of the foregoing laser stabilizer can provide a monotone increase of temperature of the sample/substrate at any desired rate. Because of this, chemical/physical (exothermal and endothermal) processes such as destruction, decomposition, phase exchange, and combustion, can be more easily investigated using the process and system of the present invention.

The present invention is quite flexible in its applications due to its accuracy and efficiency. One particular application can be the design of an incinerator for hazardous waste materials. The process and system of the present invention can be used to help design the incinerator by first analyzing the type of waste to be thermally destroyed. Thermal analysis with the system of the present invention would permit one to design an overall effective process which could include necessary pretreatments, etc. and a particularly effective temperature regime for the specific waste to be incinerated. The overall process can be designed for maximum burn, while also limiting the off-gases. In fact, in a preferred embodiment, the off-gases created during the sampling can also be analyzed in accordance with conventional methods, such as gas chromatography. By studying the offgases generated by a sample throughout a temperature regime, one can design a temperature regime that not only maximizes burn, but also avoids environmentally obnoxious gases. Thus, the process of the present invention can be used to refine a process to optimize the output for environmental purposes.

While the present invention can be used in helping to design an overall process, it can also be used to monitor and help run a continuous process. By sampling waste (or any substance) as it is being continuously fed to an incinerator, the analysis of the waste can provide instructions to a central control system to alter the temperature regime in order to maximize the efficiency of the incinerator for the particular waste being incinerated. This is particularly applicable in those instances where different types of waste may be fed on a continuous basis into an incinerator.

The method and system of the present invention can also be used to help improve the technology of a manufacturing process. By sampling the product and analyzing it, one may be able to ascertain the necessary adjustments in the manufacturing process, either on a batch or a continuous basis, in order to maximize the quality of the final product. Integration with a neural computer network can facilitate such optimization.

The invention will now be illustrated in greater detail by the following specific examples. It is understood that these examples are given by way of illustration and are not meant to limit the disclosure of the claims to follow. All percentages in the examples, and elsewhere in the specification, are by weight unless otherwise specified.

EXAMPLE 1

Gas/solid system: Destruction of ozone inside activated carbon.

A sample of activated carbon was saturated with ozone in a vessel prior to the beginning of the experiment. The limiting capacity of the activated carbon for ozone was 0.1–0.6 g/g, depending on the type of carbon. The ozone was prepared from technical oxygen in an ozonator with a barrier discharge.

In the following expression, N is the number of molecules of absorbed material per unit volume of carbon, m is the order of the reaction, and k(T) is the rate constant for the process which depends on the sample temperature.. This quantity is expressed in terms of the chemical reaction time as:

$$k(T) = 1/\tau N^{m-1}$$

The density of molecules of the absorbed material is conveniently represented in the following form:

$$N = x \rho N_o / M$$

where x is the amount of absorbed material in grams of absorbed material per gram of absorber, $\rho$ is the density of the absorber, $N_o$ is Avogrado's number, and M is the mass of a molecule absorbed material expressed in atomic mass units.

The formulas given above were used to analyze the experimental dependencies T(t) obtained by heating the samples of activated carbon containing ozone in accordance with the method and system of the present invention as described in connection with FIGS. 1–3. In some cases a thermal explosion of ozone was observed, which practically corresponds to a vertical slope on experimental T(t) plots. This effect occurs during rapid heating of the sample over times much less than the characteristic dissociation time for ozone, which can be done in practice using laser heating of the reactor. A calculation of k(T) with different amounts of absorbed ozone showed that the ozone dissociation reaction proceeds with an order m close to 2 in the temperature range 290°–525° K. The temperature dependence of the rate constants obtained for this process is shown in an Arrheniux approximation below over the temperature range 290°–525° K.:

$$k(T) = (1.9 \pm 1.0) 10^{-16} \exp[-(5600 \pm 600)/T] cm^3/sec$$

The specific energy content per unit mass of ozone according to the experimental data was determined to be 2.2±0.4 kJ/g.

EXAMPLE 2

Liquid/solid system: Destruction of nitrocompounds in activated carbon.

During operation with nitromethane, nitrobenzene, and nitrocumene, a sample of activated carbon was impregnated with a small amount of liquid, i.e., up to 0.2 g/g carbon. Preliminary experiments made it possible to determine the fraction of the liquid remaining in the sample as a result of the preparations for the measurements (pumping and holding at a pressure of $5 \times 10^{-3}$ MPa for 3 min).

In the studies of the dissociation of nitromethane absorbed by activated carbon, the amount of absorbed nitromethane was varied over the range of 0.05–0.2 g nitromethane per gram of carbon. During preparation of the measurements the samples were pumped down, and kept in a nitrogen atmosphere at a pressure of $5 \times 10^{-3}$ MPa for 3–4 min. To register the change in the amount of absorbed nitromethane with time during retention, a special series of experiments was conducted under corresponding conditions. The characteristic sample heating temperatures and the times at which they were attained differ negligibly for nitromethane, nitrobenzene, and nitrocumene.

TABLE 1

| Possible processes for dissociation of $CH_3NO_2$ | Q/m, kJ/g |
|---|---|
| $CH_3NO_2 \rightarrow CO_2 + 3/5\ H_2 + 1/2\ N_2$ | 5.2 |
| $CH_3NO_2 \rightarrow CO + H_2O + 1/4\ H_2 + 1/2\ N_2$ | 4.5 |
| $CH_3NO_2 \rightarrow 1/4\ CO_2 + 3/4\ C + 3/2\ H_2O + 1/2\ N_2$ | 6.5 |
| $CH_3NO_2 \rightarrow 1/2\ CO + 1/2\ C + 3/2\ H_2O + 1/2\ N_2$ | 5.6 |
| $CH_3NO_2 \rightarrow 5/8\ CO_2 + 3/4\ H_2O + 1/2\ N_2 + 3/8\ CH_4$ | 6.2 |
| $CH_3NO_2 + 1/4\ C \rightarrow 2CO + 3/4\ CH_4 + 1/2\ N_2$ | 3.3 |
| $CH_3NO_2 + \rightarrow 1/2\ C_2H_6 + 2\ CO + 1/2\ N_2$ | 3.1 |

Taking the variation in the mass of $CH_3NO_2$ into account, the specific energy content per unit mass of nitromethane according to the experimental data is as follows:

$$Q/m = 6.1 \pm 1 kJ/g.$$

Table 1 shows data on the energy release of possible dissociation processes for nitromethane, calculated using the thermodynamic parameters of the work. A comparison with our results indicates that the primary heat release is associated with the formation of carbon dioxide.

Note that during dissociation of nitromethane, nitrobenzene and nitrocumene in activated carbon, evaporation of these substances as the sample is heated plays a role in heat transfer. Thus, in analyzing the data we have introduced a correction for this process. For this purpose, we chose regimes in which there is negligible dissociation of the absorbed substance, and the parameters responsible for its evaporation were evaluated. These data were introduced later as a correction in evaluating the dissociation parameters.

The analysis of the experimental data showed that in this range of temperatures the dissociation of nitromethane, nitrobenzene, and nitrocumene proceeds with an order close to 2.

TABLE 2

| Composition | Formula | $E_a(K)$ | $K_o, 10^{-17}, cm^3 sec$ | Temper. °K. | Q/m, kJ/g |
|---|---|---|---|---|---|
| Nitromethane | $C_3NO_2$ | 4800 ± 500 | 2.5 ± 1.2 | 350–525 | 6 ± 1 |
| Nitrobenzene | $C_8H_5NO_2$ | 4700 ± 400 | 7 ± 3 | 370–520 | 2.3 ± 0.3 |
| Nitrocumene | $C_8H_{11}NO_2$ | 4000 ± 300 | 1.1 ± 0.2 | 370–520 | 2.1 ± 0.4 |

Averaging was done over all the experimental data.

Table 2 shows the parameters for the dissociation rate constant represented in the form $$k(T)=k_o \exp[-Ea/T]$$

These results were obtained by analyzing the data for the individual measurements. The specific heat release during dissociation of nitrobenzene and nitrocumene per unit mass of absorbed material is 2.3±0.3 and 2.1±0.4 kJ/g for nitrobenzene and nitrocumene, respectively.

The dissociation rate constants for nitrobenzene and nitrocumene in activated carbon are the same to within the error limits of the experiment over the temperature range that was investigated. This indicates that the mechanism for the process is the same. Evidently, dissociation is controlled by the interaction of the nitro-group with a benzene ring. The existence of the $(CH_3)_2CH$ group in nitrocumene does not manifest itself in the chemical process. This is also confirmed by the equal amounts of heat release in dissociation of nitrobenzene and nitrocumene.

EXAMPLE 3

Destruction of Sulphur Compounds in Heavy Fuel Oil

Liquid fuels are generally blends of many hydrocarbons with widely different physical and chemical properties. The understanding of the combustion characteristics of multi-component liquid fuels is therefore of great importance in many practical applications.

Figure 4:
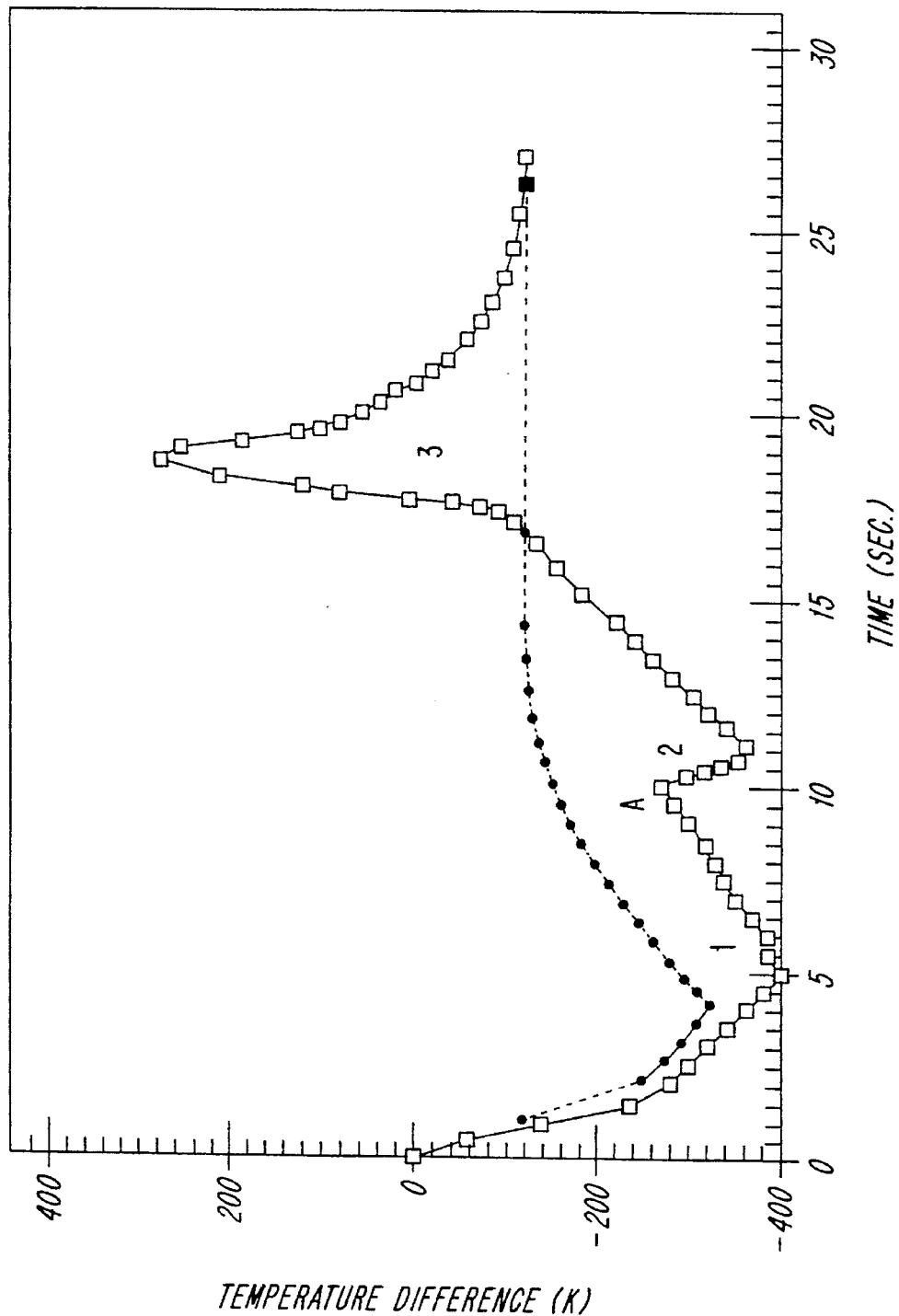
FIG. 4 is a graphical representation of the temperature dependence of a heavy fuel oil sample during heating.
Figure 5:
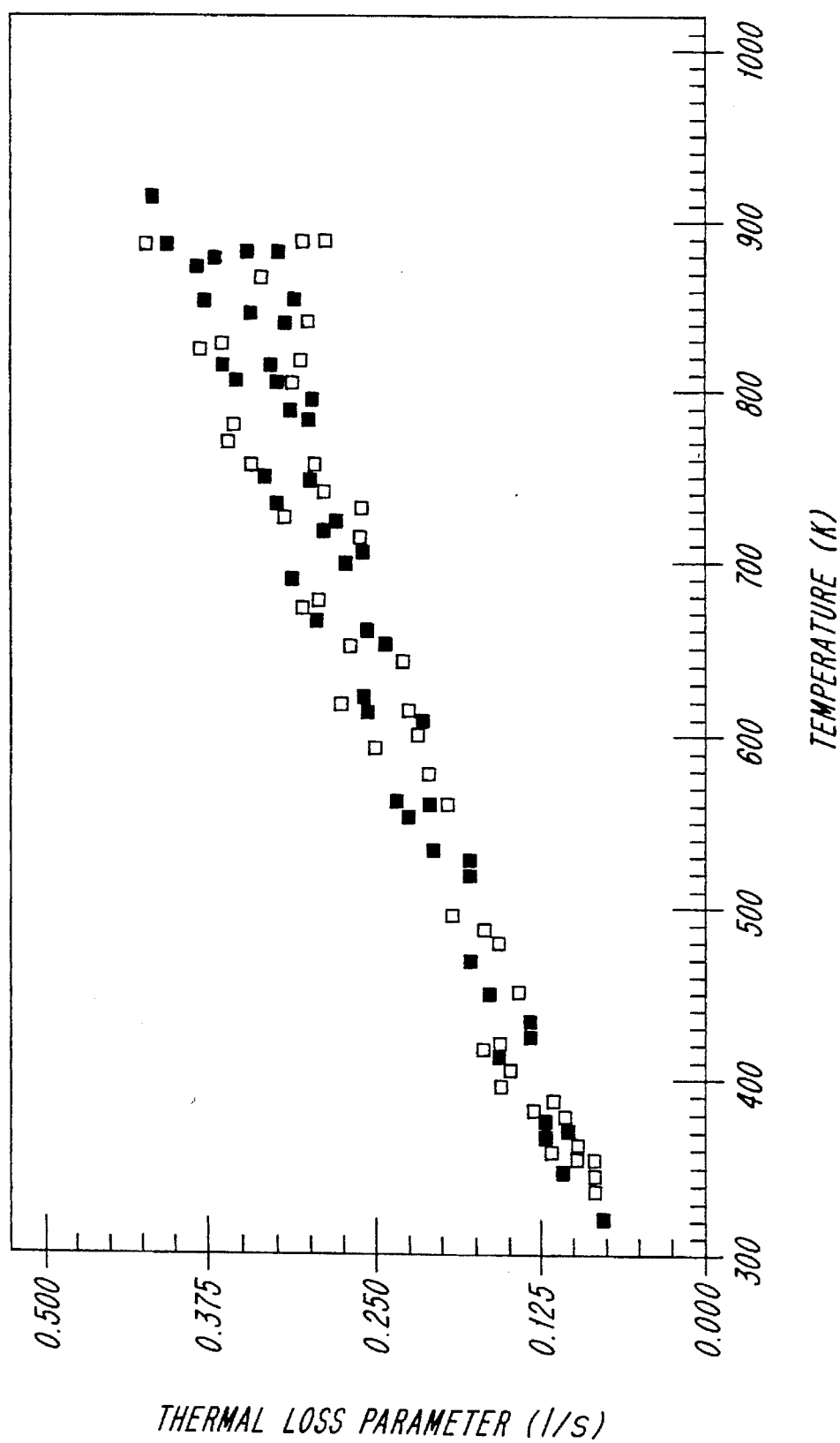
FIG. 5 is a graphical representation of the experimental dependence of the heat loss parameter $\lambda$ with regard to temperature when the investigated sample comprises heating fuel oil.

One conventional fuel, heavy fuel oil (HFO), has been the subject of investigations focusing on the determination of its combustion characteristics. FIG. 4 shows the temperature dependence of the sample during heating. We note that the HFO is a mixture of numerous hydrocarbons as well as sulphur containing compounds. The conditions of evaporation and combustion of each constituent hydrocarbon species are different. In practical experiments three stages are distinguished, which we designate as evaporation, phase transition and combustion. Since evaporation and phase transition also occur in the inert medium of nitrogen, they can be distinguished and observed independently of the combustion process. In accordance with the discussion above, the determination of heat loss for the parameter, $\lambda$, was made by measuring the rate at which the sample/substrate temperature relaxed to the thermostat temperature after laser heating. In order to do this, provisions were made for additional heating of the sample by a laser beam passing through an opening in the upper part of the reactor. FIG. 5 shows the temperature dependence of the heat loss parameter on an investigated sample of HFO. Each symbol is the result of an independent measurement. The experimental data are presented for copper and nickel substrates. The experimental data presented in the figure are in good correlation. The best-fit curve is approximated by the relation:

in the temperature region of 350°–920° K. An analysis of these results gives the following model of a general scheme of decomposition of sulfur compounds:

$$(C_nH_{2n+1})S \rightarrow C_nH_{2n+1}SH + C_nH_{2n} \rightarrow H_2S + C_nH_{2n}$$

The final reaction products are one molecule of hydrogen sulfide and two olefinic molecules. The process of the second stage was observed for sample masses greater than $5 \times 10^{-3}$ g corresponding to (for a substrate diameter of 0.3 cm) a thickness of 100 μm.

From our base measurement we conclude that during the heating of HFO there occurs the three distinct processes of evaporation, decomposition, and combustion. Decomposition can be observed for drops bigger than 100 μm in diameter. Considering the different chemical and physical properties of $(C_nH_{2n+1}SH)$ and $(H_2S)$, such as, for instance, mobility and reactivity, one can obviously find conditions for which one can reduce $SO_2$ and then $SO_3$ as a product of combustion of HFO. The measured parameters for each stage presented in this study can be used in the appropriate calculations for improving the environmental conditions relating to the combustion of HFO.

The second stage process, i.e., phase transition, commenced at 705±14° K., whereupon there was a sharp reduction of temperature by approximately 100° K. During this stage, the absorbed specific heat was (0.33±0.04) kJ/g, and change in mass measured to be 39.6% of total. This phase change process occurs faster than the sample evaporation. Furthermore, the second stage had an absorbed power of 0.4 kW which is a few times higher than that of the first stage (0.1 kW). Table 3 presents experimental data obtained from the measurement of the sample mass $(8.8\pm0.9)10^{-3}$ g. As can be seen, the reliability of the results is supported by the statistical consistency of the data.

TABLE 3

| Gas press., $N_2$, kPa; | I stage %, of weight* | I stage, kJ/g; | Thresh. Temperature, K.** | II stage %, of weight; | II stage kJ/g; | Total absorb. heat, kJ/g; |
|---|---|---|---|---|---|---|
| 5 | 29 | 0.13 | 698 | 52 | 0.32 | 0.48 |
| 5 | 36 | 0.16 | 693 | 42 | 0.30 | 0.47 |
| 10 | 31 | 0.18 | 706 | 43 | 0.32 | 0.62 |
| 10 | 38 | 0.16 | — | 41 | 0.28 | 0.44 |
| 10 | 30 | 0.22 | 681 | 44 | 0.34 | 0.75 |
| 17 | 37 | 0.24 | 716 | 43 | 0.36 | 0.71 |
| 17 | 43 | 0.25 | 730 | 42 | 0.43 | 0.72 |
| 25 | 43 | 0.33 | 720 | 28 | 0.28 | 0.88 |
| 25 | 38 | 0.22 | 681 | 36 | 0.36 | 0.65 |
| 35 | 49 | 0.33 | 719 | 31 | 0.38 | 0.80 |
| 35 | 49 | 0.34 | 708 | 25 | 0.30 | 0.99 |
| AVERAGE | 38 ± 5 | 0.23 ± 0.06 | 705 ± 14 | 39 ± 6 | 0.33 ± 0.04 | 0.68 ± 0.14 |

*—Portion of weight evaporated HFO.
**—Threshold temperature between I and II stages.

The analysis of these results is as follows:

The evaporation of molecules of fuel compounds in temperature range 350°–700° K. occurs by the scheme:

$$C_6H_8 \text{ (liquid)} \Rightarrow C_6H_8 \text{ (gas)} = 0.30 \text{ kJ/g}$$

The last term is the requisite endothermic heat absorbed.

Near the temperature range 705(±14)° K. in addition to evaporation, the following process of decomposition of sulfur compounds occurs:

$$C_9H_{19}SH(gas) \Rightarrow H_2S \text{ (gas)} + C_9H_{18} \text{ (gas)} + 0.76 \text{ kJ/g}$$

$$C_6H_{11}SH \text{ (liquid)} \Rightarrow H_2S \text{ (gas)} + C_6H_{10} \text{ (gas)} + 1.09 \text{ kJ/g}$$

This model is justified by our measurements since the specific heat absorption at two stages was (0.68±0.11) kJ/g.

Combustion of the HFO was investigated in oxygen for pressures between (4–27) kPa. Substantial rates of combustion began at temperatures near 750° K. Based on the experimental data, the combustion process consumed 26±10% by mass of fuel. See Table 3. The rate of heat evolution during combustion was determined from the experimental dependence T(t) by the equation described in (VM); 2) combustion of the VM 3) heating of the coke residue to ignition; 4) combustion of the coke residue. In our experiment we distinguished and investigated the first two stages.

Since the VM (as in the case of HFO) consists of a number of various hydrocarbons, the conditions for evaporation and combustion of each sort of hydrocarbon are different. In a practical experiment two fractions are distinguished, which we designate as "light" and "heavy". The light fraction evaporates and under our conditions this fraction does not burn, thus determining the following evaporation parameters. In Table 4 these parameters for studied coals are shown. It is assumed that the concentration of light fraction is determined by the equation: $dC/dt = -C/\tau$, where C (0<C<1) is the concentration in the relative units, and $\tau$ is the time constant of the process. These characteristics were determined by comparing the time dependencies of sample temperature in the buffer gas (nitrogen) over the temperature ranges (Table 4) in the presence and absence of the light fraction, and on the basis of the sample weight before and after evaporation of the light fraction.

TABLE 4

| Type of coal and size mm | content of VM (%% w/w) | Temperature K.; | Time constant $\tau$, sec; | The heat absorbed per unit mass, J/g |
|---|---|---|---|---|
| Kuznetsk, 0.4–0.5; | 14 ± 2 (21)* [1.8 ± 0.2]** | 430–720 | 23 ± 3 | 29 ± 5 |
| Ekibastus, 0.3–0.5; | 24 ± 5 (24) [4.0 ± 0.7] | 430–700 | 28 ± 5 | 65 ± 16 |
| Podmoscow brawn, 0.3–0.5 | 65 ± 9 (48) [8.1 ± 2.0] | 370–600 | 34 ± 3 | 126 ± 25 |
| Anthracite*** 0.3–0.5; | 3 ± 1 (4) | 310–560 | 15 ± 2 | 29 ± 3 |

*—Reference data;
**—Light fraction part;
***—In this case the VM is not distinguished into fractions.

Example 1. It was assumed that the rate of heat evolution could be approximated by the Arrhenius relation:

$$q(T) = (3.5 \pm 1.5)10^5 \, P^n{}_{O_2} \exp[-(9500 \pm 1500)/T] \text{ W/g}$$

$$(750 \leq T \leq 1300) \text{ K}$$

$$(4 \leq P_{O_2} \leq 27) \text{ kPa}$$

Where $P_{O_2}$ is the pressure of oxygen. Consider the preexponential term of $P^n{}_{O_2}$. An analysis of data: the dependence of the rate of heat evolution on temperature for various pressures of oxygen, gives an exponent, n=(1.4±0.3).

A competition between the combustion of HFO combustion and diffusion of the fuel molecules from the reaction zone (as justified by chromatographic analysis) was performed after combustion in pure oxygen and oxygen-nitrogen mixtures. The concentration of CO was insignificant in comparison to $CO_2$. The probability of combustion of a gas phase fuel molecule in pure oxygen (at 27 kPa) is 2.6 times higher than that within an oxygen-nitrogen mixture.

EXAMPLE 4

Ignition and explosion of coals at low temperatures.

For engineering calculations, the total combustion process of a coal particle is conventionally divided into four stages:
1) heating of the particle to ignition of the volatile matter The heavy part of the VM evaporates at higher temperatures, where combustion and heat evolution become appreciable. An evaporated molecule of the heavy fraction can undergo oxidation, or it can leave the reaction zone. Heat evolution occurs only in the former case. Therefore, by comparing the total heat evolution in various cases we can determine the probability of an evaporated molecule taking part in the chemical reaction.

In the case of relatively high temperatures, a portion of the evaporated heavy fraction took part in the reaction of combustion. The combustion rate was determined and approximated by the relation $$q(T) = Q_o C_o / \tau(T) = q_o EXP[-Ea/T]C_o$$

where $C_o = [Q_o - S(t)]/Q_o$; $Q_o$—total specific energy content; S(t)-observed heat evolution at time t. Since the rate of heat evolution is dependent on oxygen partial pressure, and we consider preexponential factor $q_o - p^m O_2$, where $P_{O_2}$—partial pressure oxygen, n—order.

The rate of combustion of coals VM at different pressures of oxygen let us obtain the magnitude of n.

Figure 6:
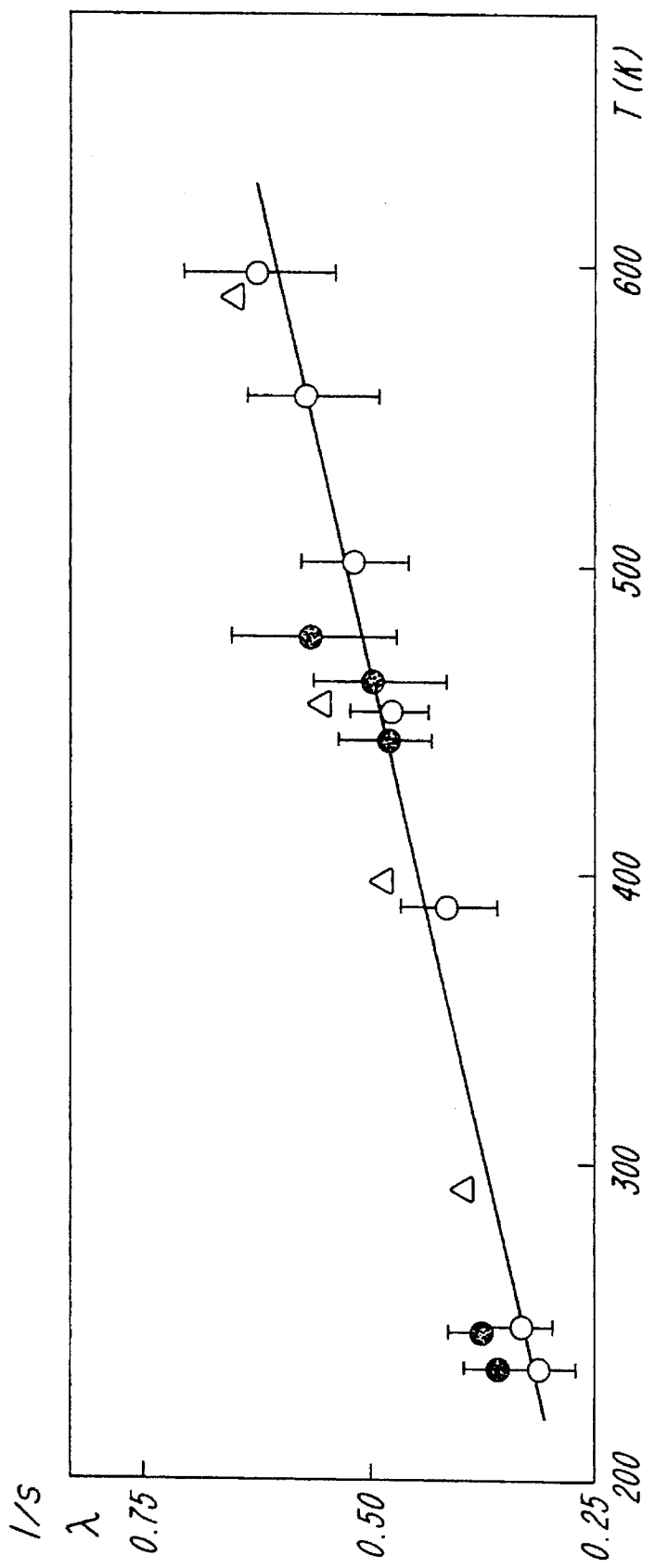
FIG. 6 is a graphical representation of the experimental dependence of the heat loss parameter $\lambda$ with regard to temperature when the investigated sample comprises different types of coal.

In accordance with previous discussions, the determination of heat loss for the parameter, $\lambda$, was made by measuring the rate at which the sample/substrate temperature relaxed to the thermostat temperature after laser heating. In order to do this, provisions were made for additional heating of the sample by a laser beam passing through an opening in the upper part of the reactor. FIG. 6 shows the temperature dependence of the heat loss parameter when investigated samples were different types of coal. The experimental data are presented for copper and nickel substrates. The results are in good correlation. The best-fit curve is shown as a line.

Appropriate relations for rates of combustion of VM matter, for partial pressure oxygen in region (4–27) $10^3$ Pa are:

1. Kuznetsk coal, with size of particles 0.4–0.5 mm.

$$q(T)=(1.1\pm 0.3)10^8 p^{1.6} o_2 EXP[-(17100\pm 2000)/T]W/g \qquad (13)$$

690K<T<810K

2. Ekibastus coal, with size of particles 0.3–0.5 mm.

$$q(T)=(0.9\pm 0.3)10^6 p^{2.1} o_2 EXP[-(14500\pm 1500)/T]W/g \qquad (14)$$

660K<T<810K

3. Podmoscow coal, with size of particles 0.3–0.5 mm.

$$q(T)=(7.2\pm 3.5)10^9 p^{2.1} o_2 EXP[17100\pm 2000)/T]W/g \qquad (15)$$

570K<T<720K.

The dependence of the ignition temperature of VM with regard to the concentration of it for different types of coals shows that due to an increase in the concentration of VM the ignition temperature is decreased (see Table 5).

TABLE 5

| Type of coals and size, mm | VM, % (w/w) | Ignition T,K | Inter. surface are, $m^2/g$ |
|---|---|---|---|
| Kuznetsk, 0.4–0.5 | 14 ± 2 | 690 ± 10 | <10 |
| Ekibastus, 0.3–0.5 | 24 ± 5 | 660 ± 10 | <10 |
| Podmoscow brawn, 0.3–0.5 | 65 ± 9 | 560 ± 10 | <100 |
| Anthracite, 0.3–0.5 | 3 ± 1 | 850 ± 50 | <1 |
| Charcoal BAU, $10^{-2}$–0.5 | 9 ± 2 | 570 ± 10 | 700 |

There is dependence on the interior surface of porous coals.

EXAMPLE 5

Emissivity of Materials

The investigation of physical and chemical properties of materials at high temperatures requires information on the emissivities of the materials in order to determine temperature. For example, the emissivity of materials is useful in different fields such as chemical, energy, and geophysics. The temperature is typically determined in such studies by measuring the thermal radiation spectrum of the material (Y. S. Touloukian and D. P. De Witt, *Thermal Radiative Properties of Metallic Elements and Alloys* I-FI/Plenum, New York, 1970). Precision in determination of the temperature depends in part on the accepted model of thermal emission, i.e., black body, gray body or non-gray body. In the case of a non-gray body, the spectral dependence of the emissivity is considered. However, there is almost no data, especially at high temperatures, in the literature about non-gray body emissivities of many materials (*CRC Handbook of Chemistry and Physics*, 71st Edition 1990–1991, p. 10–282).

Figure 7:
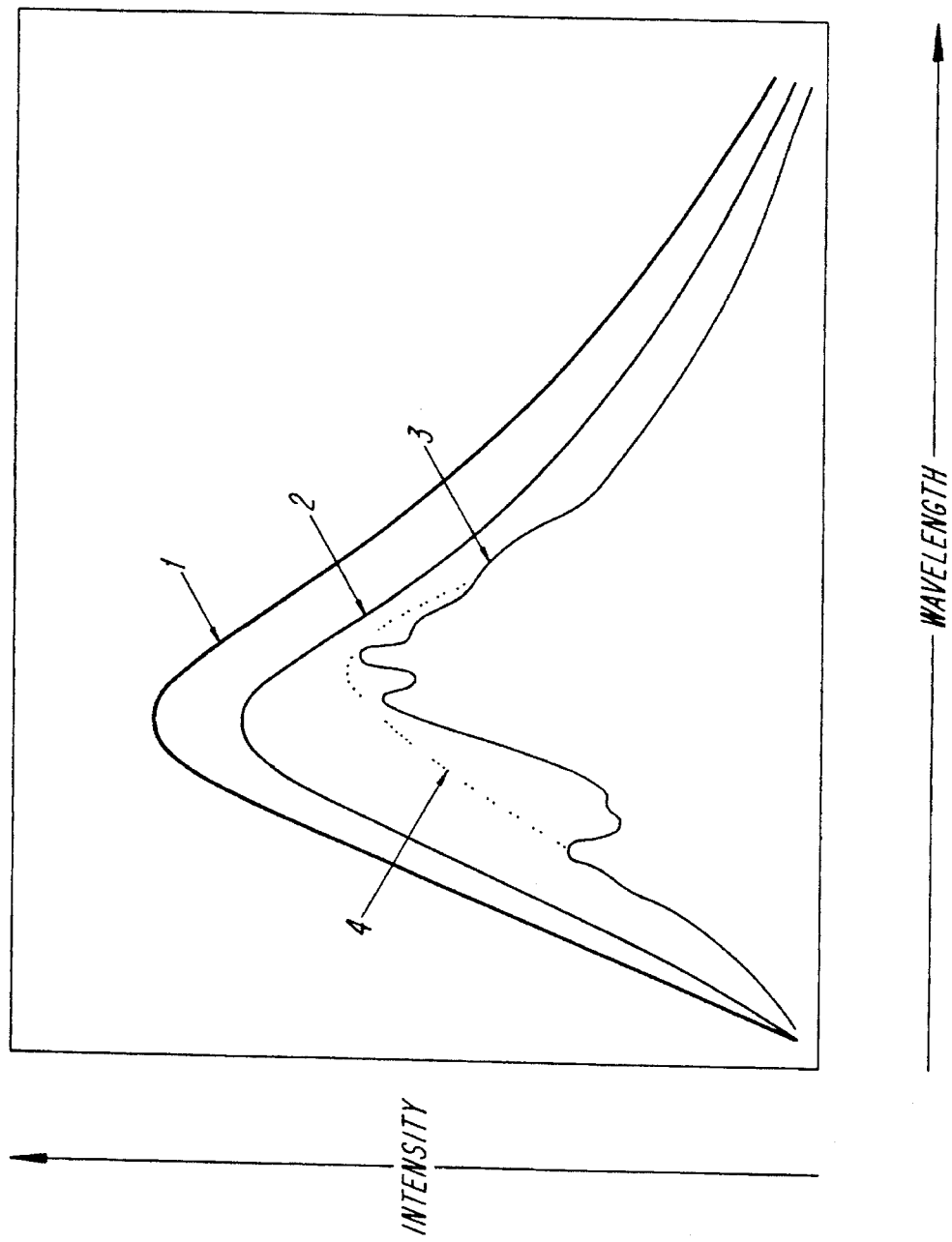
FIG. 7 is a graphical representation of the radiation spectrum of different materials at the same temperature.

The process and system of the present invention have been used for the determination of real emissivities of materials over a wide temperature range of 500° to 2600° K. FIG. 7 is a schematical representation of the radiation spectrum of different materials at the same temperature. The spectrum associated with the emissivity determined by the proposed laser driven thermal reactor is indicated by the broken line.

The emissivity of the materials determined by this method accurately yields the actual emissivity because there are no preliminary assumptions about the spectral distribution of the emissivity of the sample material: e.g., black body, gray body or non-gray body.

The foregoing examples demonstrate that the method and system of the present invention are useful in determining the corresponding parameters and conditions of processes involving multiphase systems, the decomposition of ozone and nitrocompounds, the destruction of sulfur compounds in heavy fuel oil, and in appraisals of the explosion hazards involved in coal mining. Once the parameters of the process have been determined and a chromatographic analysis of the products is made, a mathematical model can be derived which gives the phenomenological description of the process. This description of the process can be used in designing a most efficient and effective process. Special applicability is seen for hazardous waste stabilization.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A method for the thermal analysis of a substance which comprises
   (i) placing a sample of the substance on a thermally conductive substrate in a reactor with the substrate being suspended on a temperature sensor and positioned at the center of the reactor,
   (ii) heating the reactor with laser beams of equal intensity from opposing sides;
   (iii) measuring the reactor and gas temperature during the heating; and
   (iv) additionally heating the sample and substrate to a temperature above the reactor temperature and measuring the rate at which the sample and substrate temperature relaxes to the reactor temperature.

2. The method of claim 1, wherein the additional heating of the sample and substrate to a temperature above the reactor temperature is achieved by a laser beam which is focused on the sample and substrate.

3. The method of claim 2, wherein the laser beam focused on the sample and substrate is split from one of the laser beams used to heat the reactor.

4. The method of claim 2, wherein the laser beam is focused on the sample and substrate from above the sample.

5. The method of claim 1, wherein the heat loss parameter is determined using the following relationship:

$$T-T_o=(T_m-T_o)(1-exp[-\lambda(t-t_o)]),$$

where T, $T_o$ and $T_m$ are temperature, stationary temperature before additional heating, and maximum stationary temperature due to additional heating respectively; $\lambda$ is the heat loss parameter; and t is current time and $t_o$ is the time when additional heating was started.

6. The method of claim 1, wherein the additional heating of the sample and substrate is to a temperature at least 10° K. above the reactor temperature.

7. The method of claim 6, wherein the additional heating of the sample and substrate is to a temperature in the range of from 10°–50° K. above the reactor temperature.

8. The method of claim 1, wherein the measurement of the reactor and gas temperatures and the rate at which the sample and substrate temperature relaxes to the reactor temperature are all fed into a computer.

9. The method of claim 1, wherein the reactor is spherical and the substrate is of a circular shape.

10. The method of claim 9, wherein the ratio of the diameter of the spherical reactor to the ratio of the diameter of the substrate is greater than 2.5.

11. The method of claim 9, wherein the reactor comprises oxidized copper or nickel and the substrate is comprised of copper or nickel.

12. The method of claim 1, wherein the reactor comprises a material which fulfills the relationship $$\beta/\alpha > 1$$

wherein $\beta$ is the coefficient of spectral absorption in the fixed wavelength of the laser beam and $\alpha$ is the integral hemispherical emissivity.

13. The method of claim 1, wherein the laser beams used for heating the reactor and the sample are a wavelength of 1.055–1.065 microns.

14. The method of claim 13, wherein the laser is a neodymium laser.

15. The method of claim 1, which further comprises that
the additional heating of the sample and substrate to a temperature above the reactor temperature is achieved by a laser beam focused on the sample itself;
the reactor being spherical and the substrate being of a circular shape, with the ratio of the diameter of the spherical reactor to the ratio of the diameter of the substrate being greater than 2.5;
the reactor being comprised of a material which fulfills the relationship $\beta/\alpha > 1$ wherein $\beta$ is the coefficient of spectral absorption in the fixed wavelength of the laser beams and $\alpha$ is the integral hemispherical emissivity; and
the laser beams used for heating the reactor and the sample are of a wavelength of 1.055–1.065 microns.

16. The method of claim 15, wherein the additional heating of the sample and substrate to a temperature above the reactor temperature is to a temperature at least 10° K. above the reactor temperature.

17. The method of claim 16, wherein the analysis utilizes gas chromatography.

18. The method of claim 15, wherein the additional heating of the sample and substrate is to a temperature from about 10°–50° K. above the reactor temperature.

19. The method of claim 15, wherein the intensity of the laser beams used for heating the reactor is stabilized by a control system.

20. The method of claim 1, wherein the method further comprises analyzing the off-gases obtained upon heating the sample.

21. The method of claim 1, wherein the intensity of the laser beams used for heating the reactor is controlled and stabilized by a control system.

22. The method of claim 1, wherein the sample comprises waste material, solid or liquid fuel, or other solid substances for analysis.

23. A process for controlling waste destruction which comprises thermally analyzing the waste to be destroyed by the process of claim 1 prior to destruction, determining the temperature regime of destruction based upon the thermal analysis, and then destroying the waste based on the temperature regime determined.

24. The process of claim 23, wherein the process further comprises analyzing the off-gases generated during the thermal analysis and including the analysis of the off-gases in the determining of the temperature regime.

25. The process of claim 24, wherein the thermal analysis and off-gas analysis are conducted on samples taken from a continuous stream of waste material being fed to an incinerator, and the information obtained from the thermal analysis and off-gas analysis is used to continuously adjust the temperature regime used in the incinerator through integration with a neural network.

26. A method for the thermal analysis of waste material which comprises
(i) placing a sample of the waste material on a circular substrate in a spherical reactor with the substrate being suspended on a temperature sensor and positioned at the center of the reactor,
(ii) heating the spherical reactor with laser beams of equal intensity from opposing sides, wherein the intensity of the laser beams is stabilized by a control system;
(iii) measuring the temperature of the spherical reactor and surrounding gas temperatures during the heating;
(iv) additionally heating the waste material sample and substrate to a temperature at least 10° K. above the reactor temperature and measuring the rate at which the sample and substrate temperature relaxes to the reactor temperature, with the heating being achieved by a laser beam focused directly on the waste material sample and substrate itself; and
(v) feeding the measured information into a computer.

27. The method of claim 26, wherein the ratio of the diameter of the spherical reactor to the ratio of the diameter of the substrate is at least greater than 2.5.

28. The method of claim 26, wherein the reactor comprises a sphere of oxidized copper or nickel and the substrate is comprised of copper or nickel.

29. The method of claim 26, wherein all of the laser beams used are from a neodymium laser.

30. A system for thermal analysis which comprises a reactor, a laser, a system which comprises a beam splitter, mirrors and lenses for a beam from the laser; a substrate and a temperature sensor, with the beam of the laser being directed by the system of the beam splitter, mirrors and lenses to provide two opposing beams of equal intensity focused on the reactor, with a third beam of the laser being focused on the sample contained on the substrate, and with the temperature sensor being capable of measuring the temperature of the reactor, sample and gas surrounding the sample.

31. The system of claim 27, wherein the third laser beam is focused on the sample from above the sample.

32. The system of claim 27, wherein the laser used is a neodymium laser.

33. The system of claim 27, wherein the system further comprises means for controlling and stabilizing the intensity of the beams received from the laser.

34. The system of claim 27, wherein the system further comprises means for analyzing the off-gases obtained upon heating the sample.

35. The system of claim 34, wherein the means for analyzing the off-gases comprises gas chromatography.

36. The system of claim 27, wherein the third beam of the laser found on the sample is positioned above the sample, the reactor is spherical and the substrate is of a circular shape with the ratio of the diameter of the spherical reactor to the ratio of the diameter of the substrate being at least 2.5;

and the laser beams used are of a wavelength of 1.055–1.065 microns.

37. The system of claim 36, wherein the laser beams are from a neodymium laser.

38. The system of claim 30, wherein the reactor is spherical and the substrate is of a circular shape.

39. The system of claim 38, wherein the ratio of the diameter of the spherical reactor to the ratio of the diameter of the circular substrate is at least 2.5.

40. The system of claim 38, wherein the reactor is comprised of a sphere of oxidized copper or nickel and the substrate is comprised of copper or nickel.

* * * * *